United States Patent [19]

Boog et al.

[11] Patent Number: 5,215,901
[45] Date of Patent: Jun. 1, 1993

[54] PROCESS FOR PRODUCING DELTA-LACTONES FROM 11-HYDROXY FATTY ACIDS

[75] Inventors: Arnoldus L. G. M. Boog; Alfons L. J. Peters; Robert Roos, all of Bussum, Netherlands

[73] Assignee: Unilever Patent Holdings B.V., Rotterdam, Netherlands

[21] Appl. No.: 908,878

[22] Filed: Jul. 7, 1992

Related U.S. Application Data

[63] Continuation of Ser. No. 553,401, Jul. 17, 1990, abandoned.

[30] Foreign Application Priority Data

Jul. 20, 1989 [EP] European Pat. Off. ........ 89201921.7
Jul. 10, 1990 [EP] European Pat. Off. ........ 90201882.9

[51] Int. Cl.$^5$ ............................................. C12P 17/06
[52] U.S. Cl. ................................... 435/125; 435/126; 435/171; 435/135; 435/146
[58] Field of Search ............... 435/134, 135, 136, 125, 435/126, 146, 148, 171

[56] References Cited

U.S. PATENT DOCUMENTS 4,560,656  12/1985  Farbood et al. ..................... 435/134

FOREIGN PATENT DOCUMENTS 0258993  9/1988  European Pat. Off.
12104  12/1989  World Int. Prop. O.

OTHER PUBLICATIONS

Tressl et al., "Formation of Lactones and Terpenoids by Microorganisms", *Flavor of Foods and Beverages*, pp. 145–168, 1985.
Utaka et al, J. Org. Chem., 52:4363–4368 (1987).
Cardillo et al, J. Org. Chem., 54:4979–4980 (1989).
Muys et al, Nature, 194(4832):995–996 (Jun. 9, 1962).
Tehara et al, Agr. Biol. Chem., 39(1):281–282 (1975).
Roffler et al, Trends in Biotechnology, 2(5):129–136 (1984).

*Primary Examiner*—David M. Naff
*Assistant Examiner*—Marian C. Knode
*Attorney, Agent, or Firm*—Cushman, Darby & Cushman

[57] ABSTRACT

The invention provides a process for producing delta-lactones useful for incorporation in flavourings and fragrances, wherein a micro-organism which is preferably acceptable for making "food grade" products and which does not metabolize delta-lactones, is cultured aerobically in a culture medium containing as the substrate, an 11-hydroxy fatty acid having an odd number $\geq 5$ of carbon atoms between the carboxyl group and the carbon atom carrying the hydroxy group. The preferred micro-organism is a *Saccharomyces cerevisiae* species. The delta-hydroxy-alkanoic acid reaction product of the process is lactonized either in the fermentation broth or after separation therefrom. Especially suitable is 11-hydroxy palmitic acid. The hydroxy fatty acid may be added either pure or as the mixture obtained by hydrolysis of an ester thereof. Enzymatic hydrolysis of such ester may be done in situ in the fermentation broth.

10 Claims, No Drawings

PROCESS FOR PRODUCING DELTA-LACTONES FROM 11-HYDROXY FATTY ACIDS

This is a continuation of application Ser. No. 07/553,401, filed on Jul. 17, 1990, now abandoned.

The invention relates to a process for producing delta-hydroxy alkanoic acids from hydroxy fatty acids having an odd number ≧5 of carbon atoms between the carboxyl group and the carbon atoms carrying the hydroxyl group through microbial fermentation, and the subsequent transformation of these delta-hydroxy-alkanoic acids into delta-lactones.

Several delta-lactones are widely used by the flavour and fragrance industry for improving the organoleptic qualities of flavourings and perfumes. For their application in flavourings it is considered advantageous to produce these lactones from natural raw materials in a process which is also considered natural. Microbial fermentation is such a process.

In *Nature*, Vol. 194, No. 4832, pages 995–996 (Jun. 9, 1962) a synthesis of γ- and δ-lactones has been described involving a microbiological reduction of γ- and δ-ketoacids, used as starting materials. As microorganisms a number of yeasts from the Candida and Saccharomyces group, some moulds like *Penicillium notatum, Cladosporium butyri* and *Cladosporium suaveolens* and several bacteria like *Sarcina lutea* are applicable. The hydroxy acids obtained after the microbiological reduction of the γ- and δ-ketoacids were extracted from the broth and lactonized at 130°–140° C. in vacuo for 1 hour. However, above method for the production of lactones is limited to the use of rather specific starting materials i.e. γ- and δ-ketoacids like δ-keto capric acid.

Further in *Agr. Biol. Chem.* 39 (1), pages 281–282 (1975) the presence of δ-lactones in the culture broth of *Sporobolomyces odurus* AHU 3246 is reported. However, said δ-lactones were only present as minor components i.e. trace amounts in the broth (2 à 3 mg of δ-lactones per 40 liters of the culture broth). Thus, the process described in the last mentioned reference is not suitable at all for the production of δ-lactones on an industrial scale.

A process was found for producing delta-lactones on an industrial scale by using a micro-organism cultured in a culture medium containing a suitable substrate for producing delta-hydroxy-alkanoic acids, wherein a micro-organism which is generally considered acceptable for making food grade products and which does not, or only very slowly, metabolize delta-lactones, is cultured aerobically in a culture medium containing a hydroxy fatty acid having an odd number ≧5 of carbon atoms between the carboxyl group and the carbon atom carrying the hydroxyl group, under such conditions and for a period of time sufficient to produce at least 0.1 g of delta-hydroxy-alkanoic acid and/or delta-lactone per kg of fermentation broth, followed by conversion of delta-hydroxy-alkanoic acid to delta-lactone at a pH below 7 and recovery of the delta lactone substantially free from the original hydroxy fatty acid.

The applicable micro-organisms are capable of effecting β-oxidation of the hydroxy fatty acids used as starting materials. Examples of such micro-organisms may be bacteria, yeasts or filamentous fungi. Preferably the process is carried out under such conditions as to produce at least 1 g of delta-hydroxy acid/deltalactone per kg of fermentation broth. Preferred microorganisms are those which metabolize δ-lactones or δ-hydroxy fatty acids much more slowly than the hydroxy acid starting materials.

The hydroxy fatty acid having an odd number ≧5 of carbon atoms between the carboxyl group and the carbon atom carrying the hydroxyl group, which is used as the substrate in the process of the invention, may be added to the culture medium in substantially pure form, but it may also be added as part of a mixture, e.g. a mixture obtained by hydrolysis of an ester of the hydroxy fatty acid. Especially suitable mixtures may be obtained by enzymatic hydrolysis of such esters. The enzymatic hydrolysis may be performed either before or after addition to the culture medium. In the latter case, a mixture of the ester and a suitable enzyme is added to the culture medium and hydrolysis takes place during the process of the invention, thereby preparing the hydroxy fatty acid substrate in situ.

The hydroxy fatty acids having preferably 8–24 carbon atoms or their esters should preferably be derived from natural sources. Suitable esters found in nature are hydroxy fatty acid glycerides and carbohydrate esters such as those found in Jalap resins derived from roots or tubercles of *Ipomoea orizabensis* (Mexican jalap), *Ipomoea turpethum* (Indian jalap), *Ipomoea batatas* (sweet potato) and *Convolvulus microphyllus*.

Thus, a suitable starting material for the process of the invention is for instance 11-hydroxypalmitic acid, either substantially pure or as present in the hydrolysis mixture of the carbohydrate ester in question. In this case the process leads to the production of delta-hydroxy-decanoic acid and ultimately to delta-decalactone. Another suitable starting material is 3,11-dihydroxy-myristic acid obtainable from hydrolysed Jalap resin (for instance Mexican Jalap), which leads to delta-octalactone. These hydroxy fatty acids all have in common that they contain 9 carbon atoms between the carboxyl group and the carbon atom carrying the hydroxyl group.

For elucidating the invention the conversion of
(a) 11-hydroxypalmitic acid into δ-decalactone and of
(b) 3,11-dihydroxymyristic acid into δ-octalactone are illustrated.

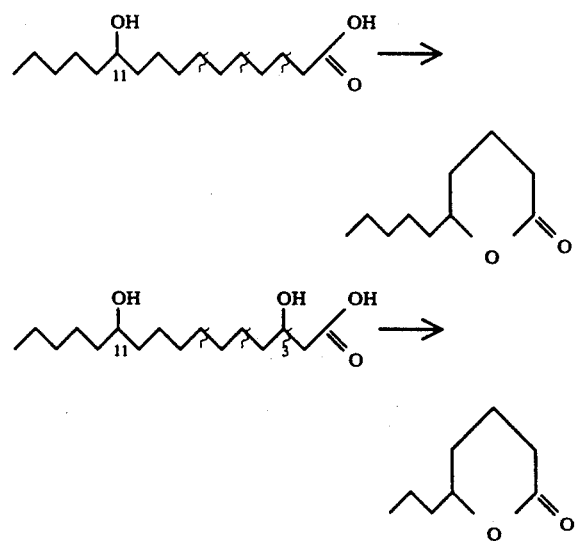

Suitable micro-organisms applicable in the process according to the invention are for instance *Saccharomyces cerevisiae* strains which may be obtained from well-known sources, such as scientific culture collections or commercial sources. Examples of such strains are:

Kitzinger Reinhefe All purposes dry yeast
Kitzinger Reinhefe Samos
Kitzinger Reinhefe Steinberg
  Paul Arauner, W. Germany.
Fermipan instant yeast
Ferotin instant yeast
  Gist-Brocades, Delft, The Netherlands.
Champagne dry yeast
Rhine wine dry yeast
Sauternes dry yeast
Tokayer dry yeast
  Souplesse Import, The Netherlands.
Vierka wine yeast "Chablis"
  Friedrich Sauer, E. Germany.
Fleischmann active dry yeast
  Standard Brands Inc., New York, USA.
Wine yeast Broerken
  Liberty Nederland, The Netherlands.
Brewers yeast
  Propps, Sweden.
Vinkwik wine yeast
  Jan Dekker, Wormerveer, The Netherlands.
Bakers yeast
  Bruggeman, Belgium.

Other suitable micro-organisms are *Sporobolomyces odorus, Rhodotorula glutinis, Aspergillus oryzae, Geotrichum Klebahnii, Yarrowia lipolytica, Hansenula saturnus, Candida guilliermondii, Candida albicans, Candida krusei, Candida parakrusei, Candida pseudotropicalis, Candida stellatoidea, Candida tropicalis, Candida rugosa* and members of the genus Pityrosporum like *P. canis, P. pachydermatis, P. orbiculare* and *P. ovale*. Specific strains of suitable microorganisms have been deposited at the "Central Bureau voor Schimmelcultures" (CBS), The Netherlands; these strains are *Candida boidinii* (CBS 7447), *Candida silvicola* (CBS 7448), *Zygosaccharomyces fermentati* (CBS 7445 and 7446), *Torulaspora delbruchii* (CBS 7443), and *Candida apicola* (CBS 7444).

The fermentation according to the invention is carried out at a pH between 3 and 9, preferably between 4.5 and 7.5, more preferably between 5 and 7.2. The temperature should be kept between 10° and 40° C., preferably between 15° and 35° C. Aeration is preferably regulated so as to keep $pO_2$ of the fermentation broth above 10% of saturation.

A suitable culture medium comprises the usual nutrients, i.e. carbon sources, nitrogen sources, inorganic salts, growth factors and trace elements. Suitable carbon sources are generally known in the art and include saccharides and saccharide-derived polyols, glycerol, organic acids such as lactic acid, citric acid, succinic acid, ascorbic acid. Among the suitable nitrogen sources are, for example, peptone, meat extract, yeast extract, corn steep liquor and amino acids. Well-balanced culture media preferably contain at least a small amount of yeast extract, which in most cases obviates the need to add vitamins, inorganic salts, trace elements and the like separately.

Particularly well-balanced culture media contain at least 0.1% w/w of yeast extract and 0.25% w/w or more of peptone. In some cases, the addition of up to 20 mg/kg of $Fe^{2+}$, e.g. as $FeSO_4$, to the culture medium may be advantageous.

The culture medium is preferably inoculated with at least 1,000 cells/kg. The hydroxy fatty acid used as substrate may be conveniently added as the only carbon source, either at the start of the culture or at a later stage, e.g. when the maximum amount of cells has been reached. It may also be added gradually, either in a fed batch-type operation or e.g. by adding a hydroxy fatty acid ester, for instance a $C_{1-6}$ alkylester, and a suitable enzyme, e.g. a lipase, to the culture medium, causing the hydroxy fatty acid to be liberated gradually during the fermentation. Either way, a total amount of at least 0.1% by weight of hydroxy fatty acid is preferably added to the culture medium.

A level of 0.1 g delta-lactone and delta-hydroxyalkanoic acid together per kg of fermentation broth is usually reached within 24–36 hours and the maximum amount will generally be reached within 10 days. In many cases this maximum will already be reached in a much shorter time. When a microorganism is used, which not itself is able to metabolize the produced lactone, the exact fermentation time is not critical since in the process of the invention the delta-lactone content does not diminish with time after reaching its maximum. Thus, the lactone is completely stable in the fermentation broth.

If desired, the micro-organism may be immobilised on a support employing a usual technique such as described in Eur. J. *Appl. Micro. & Biotech.* 15 (1982), pp. 147–152 and *Biotech & Bioeng* 19 (1977), p. 387 et seq.

To facilitate the dispersion of the substrate in the culture medium, a suitable emulsifier may be added in an amount of up to 1% w/w of the culture medium. Foaming of the fermentation broth may be prevented by the addition of conventional anti-foaming agents.

The reaction product usually consists of a mixture of delta-hydroxy-alkanoic acid and the corresponding delta-lactone. This mixture may be separated from the fermentation broth with usual techniques, as for instance illustrated in the survey article of Roffler S. R. et al. titled "In situ recovery of fermentation products", published in *Trends in Biotechnology*, Vol. 2, No. 5, 1984, pages 129–137. Examples of suitable recovery methods are the use of anion-exchange resins, for instance "Dowex 203", "Amberex 5500" and "BIORAD BIOREX 5" and the "extractive fermentation" method, i.e. extraction methods with either a suitable absorbent or with a preferably non-toxic organic solvent (see also page 132 of the last mentioned reference). Thereafter the obtained delta-hydroxy-alkanoic acid is converted to the delta-lactone in the usual way at a pH below 7. Alternatively, lactonisation may be completed in the fermentation broth by lowering the pH to below 7, preferably below 5 and mild application of heat, if necessary. The lactone is thereafter separated from the fermentation broth by for instance an extraction step and purified, if desired, by distillation.

The lactones obtained by the process according to the invention may be added to flavourings or foodstuffs, for instance products made of animal or vegetable fats such as margarins and cooking oils, either as such or dissolved in a suitable solvent or processed into a powdered product. The obtained δ-lactone has chiral properties, which makes it similar to lactones obtained from so far known natural sources like coconut. Flavouring components which may be used with the lactones according to the invention are well known in the art and are mentioned, e.g., in S. Arctander, Perfume and Flavor Materials of natural Origin (Elisabeth, N.J., USA, 1969), in T. E. Furia et al., CRC Fenaroli's Handbook of Flavor Ingredients, 2nd Ed. (Cleveland, CRC Press Inc., 1975) and in H. B. Heath, source Book of Flavors (The Avi Publishing Company Inc., Westport, Conn., 1981).

The invention is illustrated by the following Examples but is not limited thereto in any way.

EXAMPLE 1

100 ml Sterilized (20 minutes at 121° C.) culture medium in a baffled flask and consisting of 2% w/w of soya peptone (Merck 7212), 0.5% w/w of yeast extract (Difco, 0127-01) and 1% w/w of 11-hydroxy palmitic acid was inoculated with $4.10^4$ cells of Saccharomyces cerevisiae (Kitzinger reinhefe all purposes dry yeast). The substrate 11-hydroxy palmitic acid was isolated from Jalap resin ex Ipomoea orizabensis (Mexican Jalap). The pH of the culture medium was set at 6.5 with NaOH(1M) and remained constant during the whole fermentation. The broth was incubated at 28° C. on a rotary shaker (150 rpm) for 5 days.

Samples were periodically taken to determine the progress of the process. The concentration of delta-decalactone was determined after extraction with a mixture of butylacetate and acetic acid (100%) in a ratio of 90:10 (v/v), followed by separation of the layers and using GLC (Gas-liquid-chromatography).

At the end of the fermentation the broth contained 1.0 g/kg delta-decalactone. The broth was acidified with 100% acetic acid to pH 3 and extracted with butylacetate. The residue was distilled to provide the delta-decalactone in a yield of 85%

EXAMPLE 2

A fermentation was carried out using the procedure and materials described in Example 1, except that Fermipan instant yeast of Gist-Brocades, Delft, The Netherlands, was used instead of the Saccharomyces cereviseae strain mentioned. 0.75 g/kg Delta-decalactone was obtained from the broth.

EXAMPLE 3

Example 2 was repeated, but with the microorganism Yarrowia lipolytica. The highest obtained concentration of delta-decalactone during the fermentation was 0.4 g/kg.

EXAMPLE 4

Example 1 was repeated with 11-hydroxy palmitic acid isolated from Ipomoea batatas (sweet potato). The yield of delta-decalactone was 1 g/kg.

EXAMPLE 5

A fermentation was carried out, using the procedure and materials described in Example 1, except that 10 g capsul (food grade dextrine; National Starch), 0.15 g linoleic acid, 0.15 g oleic acid and 4 g lecithin were added per liter of fermentation broth. 1.5 g/kg Delta-decalactone was obtained from the broth.

EXAMPLE 6

Example 1 was repeated with a mixture of 11-hydroxy palmitic acid and 3,11-hydroxy myristic acid isolated from Ipomoea tuberosa (Brasilian Jalap). Delta-decalactone and delta-octalactone were obtained in the broth and were isolated as described in Example 1.

EXAMPLE 7

Example 1 was repeated with the ethylester of 11-hydroxy palmitic acid which acid was isolated from Ipomoea orizabenzis and converted into the ethylester derivative with ethanol. The used microorganism had sufficient esterase activity of its own. The yield of delta-decalactone was 1 g/kg fermentation broth.

We claim:

1. A process for producing a delta lactone comprising
   (i) aerobically culturing a microorganism in a nutrient medium containing assimilable sources of carbon, nitrogen, inorganic salts and an 11-hydroxy fatty acid to produce a delta hydroxy-alkanoic acid and a delta lactone;
   (ii) converting the delta hydroxy-alkanoic acid to the delta lactone; and
   (iii) recovering the delta lactone;
   wherein said culturing is carried out under such conditions and for a time sufficient to produce at least 0.1 g of the sum of the delta hydroxy-alkanoic acid and the delta lactone formed in situ from said 11-hydroxy fatty acid per kg of fermentation broth and wherein the microorganism is selected from the group consisting of Saccharomyces cerevisiae, Sporobolomyces odorus, Rhodotorula glutinis, Aspergillus oryzae, Geotrichum klebhanii, Yarrowia lipolytica, Hansula saturnus, Candida guilliermondii, Candida albicans, Candida krusei, Candida parakrusei, Candida pseudotropicalis, Candida stellatoidia, Candida tropicalis, Candida rugosa, Pityrosporium canis, Pityrosporium pachydermatis, Pityrosporium orbiculare, Pityrosporium ovale, Candida boidinii, Candida silvicola, Zygosaccharomyces fermentati, Torulaspora delbruchii, and Candida apicola.

2. A process according to claim 1, wherein the microorganism does not metabolize δ-hydroxy fatty acids or δ-lactones.

3. A process according to claim 1, wherein the hydroxy fatty acid is prepared in situ in the culture medium by adding thereto a hydroxy fatty acid ester and a suitable hydrolysis enzyme.

4. A process according to claim 3, wherein the hydroxy fatty acid ester is a glycerol ester.

5. A process according to claim 3, wherein the hydroxy fatty acid ester is a carbohydrate ester.

6. A process according to claim 1, wherein the 11-hydroxy fatty acid is 11-hydroxy palmitic acid.

7. A process according to claim 1, wherein the 11-hydroxy fatty acid is 3,11-dihydroxy-myristic acid.

8. A process according to claim 1, wherein the 11-hydroxy fatty acid is obtained by hydrolysis of a jalap resin.

9. A process according to claim 1, wherein the delta-hydroxy-alkanoic acid is converted to the delta-lactone in the culture medium, after separation therefrom or both, at a pH below 7.

10. A process according to claim 9, wherein the microorganism is Saccharomyces cerevisiae, Yarrowia lipolytica, Candida boidinii, Candida silvicola, Zygosaccharomyces fermentati, Torulaspora delbruchii, or Candida apicola and the hydroxy fatty acid is 11-hydroxy palmitic acid, the culturing being carried out at a pH below 7 whereby some of the delta-hydroxy-alkanoic acid is converted to delta-lactone in the culture medium.

* * * * *